United States Patent [19]

Leschinsky et al.

[11] Patent Number: 5,439,448
[45] Date of Patent: Aug. 8, 1995

[54] BUBBLE-FREE CONNECTOR FOR LIQUID CARRYING TUBING

[75] Inventors: Boris Leschinsky, Waldwick; Robert B. Schock, Sparta; Robert L. Wilcox, Wanaque; Clifford E. Schwartz, Maplewood, all of N.J.

[73] Assignee: Datascope Investment Corp., Montvale, N.J.

[21] Appl. No.: 162,771

[22] Filed: Dec. 8, 1993

Related U.S. Application Data

[63] Continuation-in-part of Ser. No. 5,334, Jan. 19, 1993, Pat. No. 5,312,352.

[51] Int. Cl.[6] ............................................. A61M 5/00
[52] U.S. Cl. .................................. 604/122; 604/905; 604/283
[58] Field of Search ............... 604/122, 905, 283.1, 604/284, 280, 265; 285/924, 153

[56] References Cited

U.S. PATENT DOCUMENTS

| | | | |
|---|---|---|---|
| 2,597,699 | 5/1952 | Bauer | 128/214 |
| 3,833,013 | 9/1974 | Leonard . | |
| 4,004,587 | 1/1977 | Jess . | |
| 4,143,423 | 3/1979 | Sternlieb . | |
| 4,361,380 | 11/1983 | Marazzi . | |
| 4,493,705 | 1/1985 | Gordon . | |
| 4,526,572 | 7/1985 | Donnaw et al. . | |
| 4,568,333 | 2/1986 | Sawyer et al. . | |
| 4,615,694 | 10/1986 | Raines . | |
| 4,636,196 | 1/1987 | Tsuji et al. . | |
| 4,643,713 | 2/1987 | Viitala . | |
| 4,863,452 | 9/1989 | Irmiter et al. . | |
| 5,135,264 | 8/1992 | Elliott-Moore . | |
| 5,147,298 | 9/1992 | Turner . | |

*Primary Examiner*—C. Fred Rosenbaum
*Assistant Examiner*—Perry E. Van Over
*Attorney, Agent, or Firm*—Fitzpatrick, Cella, Harper & Scinto

[57] ABSTRACT

A system and method for connecting a first fluid carrying tube and a second fluid carrying tube or tube fitting includes a first tube having a lumen therethrough and an open end, and a second tube or tube fitting having a lumen therethrough and an open end. The first tube and second tube (or tube fitting) are connected by connecting means, including a bubble elimination chamber, in a first position, wherein the lumen of the tube, the lumen of the connecting means and the lumen of the tube fitting form a fluid-tight circuit and the bubble elimination chamber is open to the circuit, to permit elimination of any bubbles in the fluid circuit to the bubble elimination chamber. The first tube, connecting means and second tube (or tube fitting) then are connected in a second position, wherein a continuous, fluid-tight, bubble-free fluid circuit is formed, and the bubble elimination chamber is closed to the fluid circuit. The connecting means may include a soft connector alone or in combination with a connector tube.

33 Claims, 7 Drawing Sheets

BUBBLE-FREE CONNECTOR FOR LIQUID CARRYING TUBING

This application is filed as a continuation-in-part of application Ser. No. 08/005,334 filed Jan. 19, 1993, now U.S. Pat. No. 5,312,352.

BACKGROUND OF THE INVENTION

1. Field of the Invention

The present invention relates generally to a method and apparatus for connecting two or more fluid carrying tubes. The method and apparatus of the present invention have particular utility for connecting blood carrying medical tubing in a continuous fluid circuit without introducing bubbles or other environmental contaminants into the tubing, but may be used for connecting any two or more fluid carrying tubes.

2. Description of the Prior Art

Extracorporeal procedures are well known. In these procedures, blood generally is withdrawn from a patient through cannulation, treated (e.g. by pumping, oxygenation, filtering, or the like), and reintroduced to the patient through cannulation. For example, in a cardio-pulmonary bypass procedure, blood may be withdrawn through cannulation at a first site upstream of an occlusion site, pumped, and reintroduced through cannulation at a second site downstream of the occlusion site.

Each of these extracorporeal procedures requires a stage of connecting one blood carrying tube, such as a cannula, to another blood carrying tube, or to another element, such as an external pump, to provide a continuous fluid circuit. This stage of the procedure requires great care in preventing introduction of air or other contaminants into the fluid circuit. In particular, air bubbles can cause embolism or other medical complications that may be harmful or fatal to the patient.

For example, in one conventional procedure, each of a cannula and a tube typically are primed with a conventional priming fluid, such as a saline-based priming solution, and then clamped at a location proximate the end portion thereof, to assure that each is filled as full as possible with such fluid. The open ends of the primed cannula and blood tube then are connected slowly under a continuous stream of solution, e.g., from an external syringe, to provide a bubble-free fluid connection. A variation of this technique may be used when the fluid circuit includes a roller-type pump. In this variation, a perfusionist rotates the pump head of the pump in a forward direction to perform a "roll-up" technique, which continuously advances priming fluid out of the blood tube during the connecting stage.

These techniques have a number of drawbacks. First, each technique requires a degree of training to make a bubble free connection. For example, in the former technique, connection under a stream of fluid may cause air entrainment, resulting in bubbles in the tubing. The latter technique is well suited to a roller-type pump, and may not be easily adapted for use with a centrifugal pump, or the like. Each of these techniques requires two people to perform the connection. Also, after completion of the connection, it often is not possible to disassemble the cannula and tubes if bubbles then are detected in the tubes. Moreover, since these techniques are not easily repeatable, they are not desirable in the case of an emergency procedure.

It is also known in the art to use a connector tube for connecting two-fluid carrying tubes at respective open ends thereof. Such a connector tube preferably is a short, rigid cylindrical tube, and may include securing structure, such as barbs, at each end thereof for rigidly and securely connecting the previously open ends of the fluid carrying tubes to form a continuous fluid channel or circuit.

An improvement on this technique includes a hard, barbed, connector tube provided with a branch or side-arm luer port. The luer port may be used for collecting and eliminating any air bubbles trapped in the fluid circuit after connection.

These techniques also have a number of drawbacks. Initially, when a connector tube is inserted in the open end of one fluid carrying tube, it functions as an extension of that tube for connecting to the second tube. Thus, this system includes all of the above-discussed drawbacks. The branches or luer fittings also have a drawback in that they introduce an element that protrudes from the fluid circuit during procedure. This protrusion may catch on surrounding objects or accidentally be broken off, resulting in inconvenience or possibly major blood loss during procedure. Moreover, these protrusions form vestiges that remain on the side wall of the connector tube of the fluid circuit. These vestiges are discontinuities that form stagnation zones in the fluid circuit that tend to cause thrombus. Thrombus can cause other medical complications that may be fatal to the patient.

SUMMARY OF THE INVENTION

The present invention overcomes these and other drawbacks of the prior art by providing a novel method and apparatus for connecting two or more fluid or liquid carrying tubes to form a continuous, bubble-free fluid channel or circuit.

In one aspect, the present invention relates to a method and system for connecting two or more fluid carrying tubes in a continuous, fluid-tight, bubble-free circuit. The system generally includes a first tube having bubble elimination means proximate to and axially displaced from an open end thereof, a second tube having an open end, and means for connecting the open ends of the first and second tubes in a first position, wherein the open ends form a fluid-tight connection and the bubble elimination means is open to a continuous fluid circuit for eliminating any bubbles from the fluid circuit, and for connecting the first and second tubes in a second position, wherein the bubble elimination means is closed to a continuous fluid-tight circuit.

In one embodiment, the bubble elimination means is a side port formed in a wall of the first tube, the second tube includes a connector portion at the open end thereof, and the connector portion is insertable in the open end of the first tube to form a continuous bubble-free fluid-tight circuit therebetween.

In this embodiment, the method of the present invention generally includes the steps of inserting the connector portion of the second tube into the open end of the first tube to the first position to form a fluid circuit, wherein the bubble elimination port is open to the fluid circuit, and then eliminating any bubbles from the fluid circuit, e.g., by venting them to, or trapping them in, the bubble elimination port. The connector portion of the second tube then is further inserted into the first tube to a second position, wherein the bubble elimination port is closed to a continuous, fluid-tight circuit.

In another aspect of the present invention, the connecting means may be a separate connector tube having one end for connecting to the open end of a first tube, and a second end for connecting to the open end of a second tube. The connecting tube may include securing means, such as barbs, at each end. The connecting tube also may have an elongated first end sequentially insertable to first and second positions within the first tube. Moreover, the elongated portion may be lubricated to facilitate insertion.

In another aspect of the present invention, the first tube may have a curved portion proximate the open end thereof, and the bubble elimination port may be located on the curved portion, at a high point thereof, to facilitate bubble elimination. In one embodiment, at least the curved portion of the first tube may be made of a flexible material, so that the curved portion of the fluid tube may conform to the configuration of a connector portion or tube when the connecting means is connected in the second position.

In yet another aspect of the present invention, the first tube may include a receiving portion located proximate the open end thereof, and the receiving portion may be pretreated for receiving the connecting means. For example, in one embodiment, the receiving portion may be prestretched. In another embodiment, the first tube may be formed of a heat sensitive material, and the receiving portion may be preheated to soften the material for receiving the connecting means.

The present invention also contemplates using a soft connector comprising a bubble elimination chamber. For example, in one aspect the soft connector includes a sleeve and a bubble elimination chamber arranged generally coaxial thereto. The sleeve may be provided with a circular cross-section for receiving a standard tube therein, and for forming an annular, fluid-tight seal therewith. The sleeve also may include a resilient lip at an end thereof, for facilitating manipulation of the sleeve relative to the tube, and for facilitating sealing. The bubble elimination chamber is in fluid communication with a lumen of the sleeve, and includes an annular port for connecting with a barb fitting to form a fluid-tight circuit.

In a preferred method for this aspect, the clinician slides the connector sleeve over an open end of a tube to form an extension of the tube, such that the tube/connector assembly includes a bubble elimination chamber in fluid communication with a lumen of the tube. Each of the tube assembly (tube with connector extension) and a barbed fitting then are primed, and the tube, the connector and the barbed fitting are connected in a first position, wherein the bubble elimination chamber is open to a fluid-tight circuit. Any bubbles in the circuit then are eliminated, e.g., by venting them to, or trapping them in, the bubble elimination chamber. Finally, the open end of the tube is inserted into an annular nip formed between the annular port of the connector and the fitting. In this manner, the open end of the barbed fitting is inserted in the open end of the tube, such that the tube, the connector and the fitting are connected in a second position, wherein the bubble elimination chamber rolls-up over the tube, and is closed to a continuous, bubble-free, fluid-tight circuit formed by the tube and the fitting.

In still a further aspect, the system of the present invention generally includes a soft connector and a connector tube for connecting a first tube and second tube. The soft connector has a generally tubular body and includes a first connecting port, a second connecting port, and a bubble elimination chamber disposed in a wall of the soft connector between the first connecting port and the second connecting port, wherein the bubble elimination chamber is in fluid communication with a lumen formed between the first and second connecting ports of the soft connector.

In this embodiment, the method of the present invention generally includes the steps of inserting the open end of the first tube into the first connecting port of the soft connector tube to form a first tube assembly, and inserting a first end of the connector tube into the open end of the second tube to form a second tube assembly. Each of the first tube assembly and the second tube assembly then is primed, preferably in a vertically inclined orientation. In a first connecting stage, the second (open) end of the connector tube is inserted into the second connecting port of the soft connector to a first position, to form an annular fluid-tight connection therebetween. In this manner, the first tube, the second tube, the connector tube, and the soft connector form a continuous fluid channel or circuit, and the bubble elimination chamber is open to the fluid circuit for collecting any bubbles located therein. In a second connecting stage, the connector tube is further inserted to a second position, wherein the first tube, the second tube and the connector tube form a continuous, fluid-tight circuit, and the bubble elimination chamber is closed by the connector tube.

In another aspect, the method of the present embodiment further may include the step of pinching the soft bubble elimination chamber during the first connecting stage, to provide a flow of prime fluid to the point of connection, to prevent formation of any bubbles in the fluid circuit during the first connecting stage.

In a further aspect, the method of the present invention may include the further step of releasing the pinched bubble elimination chamber after the first and second tube assemblies are connected in the first position, to facilitate removal of any bubbles in the fluid circuit by vacuum.

These and other attendant features and advantages of the present invention will be readily and more completely appreciated with reference to the following detailed description of several embodiments taken together with the accompanying drawings.

DETAILED DESCRIPTION OF A PREFERRED EMBODIMENT

Figure 1:
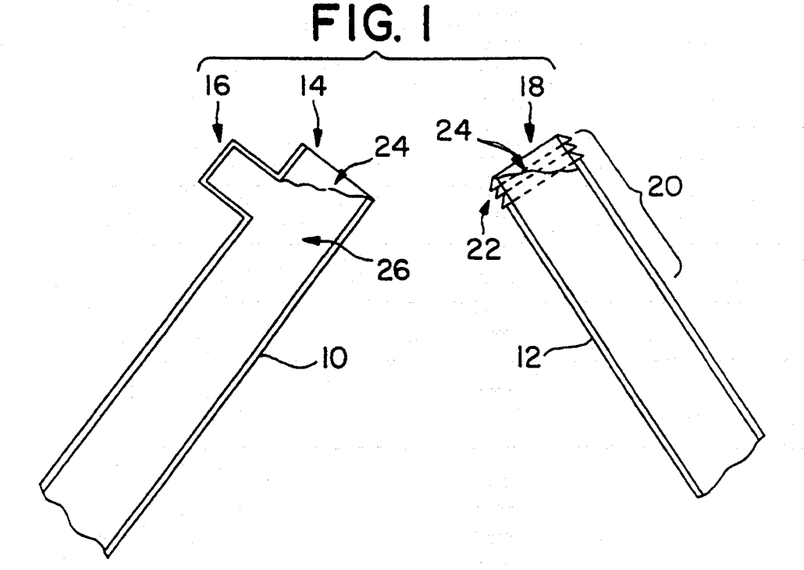
FIG. 1 is side schematic view of one embodiment of a bubble-free connector system of the present invention in an open configuration.
Figure 2:
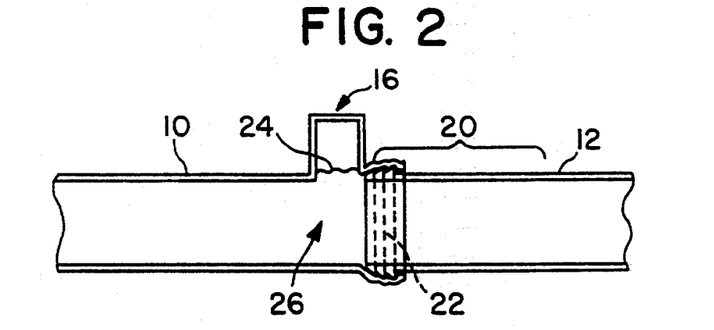
FIG. 2 is a side schematic view of the connector system of FIG. 1, wherein a connector portion of the second tube is inserted to a first position, and a bubble elimination port of the first tube is open to a fluid-tight circuit.
Figure 3:
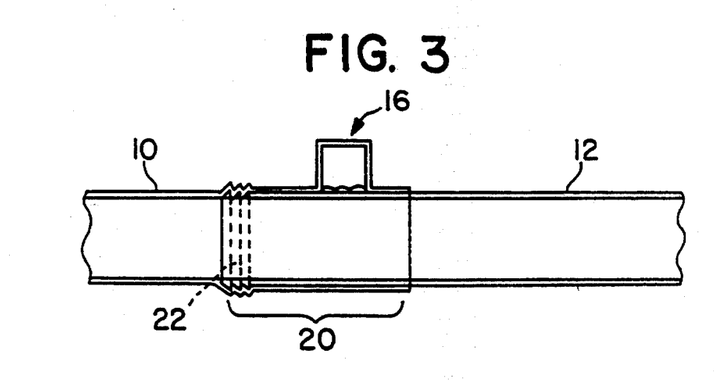
FIG. 3 is a side schematic view of the connector system of FIG. 1, wherein a connector portion of the second tube is inserted to a second position, and a bubble elimination port of the first tube is closed to a continuous, fluid-tight circuit.

FIGS. 1 to 3 illustrate in side schematic view one embodiment of a connector system of the present invention. The system generally includes a first tube 10, a second tube 12, and means for connecting the first tube 10 and the second tube 12 in a continuous, fluid-tight, bubble-free fluid circuit. More specifically, in the present embodiment, first tube 10 has an open end 14 and a bubble elimination port 16 located proximate open end 14, and axially displaced therefrom. Second tube 12 has an open end 18 and a connector portion 20 constituting the connecting means.

Each of first tube 10 and second tube 12 is composed of a conventional material suitable for carrying blood. At least one of first and second tubes 10,12 preferably is formed of a flexible plastic material, and most preferably of a clear plastic material, such as Tygon ™ tubing, so that a clinician may view the interior of the tubing to detect any bubbles therein.

In the embodiment of FIGS. 1 to 3, first tube 10 is a ⅜ inch inner diameter—9/16 inch outer diameter tube composed of polyvinylchloride ("PVC"). Bubble elimination port 16 is formed integrally with first tube 10, has a volume of about 1 cc, and is located about ¼ inch from open end 14. Second tube 12 is a ⅜ inch inner diameter—9/16 inch outer diameter tube composed of PVC, and connector portion 20 is an extension of this tube having a ⅜ inch inner diameter—9/16 inch outer diameter. Connector portion 20 preferably is about 1 inch long and includes one or more annular ridges or barbs 22 proximate open end 14 of second tube 12. For example, as shown in FIGS. 1 to 3, connector portion 20 may have 3 barbs located in a ¼ inch long portion adjacent open end 14. As will be described below, the sizing of connector portion 20 and barbs 22 is selected so as to provide a fluid-tight seal with first tube 10.

A preferred method of the present invention also will be described with reference to FIGS. 1 to 3. Initially, in a priming stage, as shown in FIG. 1, first and second tubes 10,12 are arranged in an orientation wherein the open ends 14,18 thereof are elevated, and tubes 10,12 are primed by a conventional method so that each tube is substantially filled with prime fluid 24 (see FIG. 1). Most preferably, first tube 10 is filled so that bubble elimination port 16 is at least substantially filled with prime fluid 24. Of course, this may be facilitated by rotating first tube 16 about its longitudinal axis, so that bubble elimination port 16 vertically depends from first tube 16.

Referring to FIG. 2, in a first connecting stage, connector portion 20 of second tube 12 then is inserted into open end 14 of first tube 10. Specifically, connector portion 20 is inserted into first tube 10 until it reaches a first position where first and second tubes 10,12 form a closed, fluid-tight, fluid channel or circuit and bubble elimination port 16 is open to the fluid circuit. In other words, bubble elimination port 16 is in fluid communication with the fluid circuit. In this configuration, a fluid-tight annular seal is formed between barbs 22 and the inner wall of first tube 10.

It will be appreciated that this first connecting stage or procedure generally may trap a small bubble within the fluid circuit proximate connector portion 20, and that the size of the bubble may vary for each procedure, depending on the size of the tubing and the expertise of the clinician. Although it is preferable to form the connection with a minimal sized bubble entrapped therein, it also will be appreciated that bubble elimination port 16 permits a clinician to rapidly and efficiently connect first and second tubes 10,12 without worrying about effecting a bubble free connection in the first instance. Specifically, any bubble entrapped in the fluid circuit at this time then may be eliminated by removing it to bubble elimination port 16. Of course, as a bubble is removed from the fluid circuit to port 16, it will displace an equal amount of fluid from port 16 into the fluid circuit, thereby to eliminate any bubbles in the fluid circuit.

Referring now to FIG. 3, in a second or final connecting stage, after any bubble entrapped in the fluid circuit is removed to bubble elimination port 16, connector portion 20 further is advanced into first tube 10, to a second position, wherein first and second tubes 10,12 form a continuous, closed, fluid-tight channel or circuit, and bubble elimination port 16 is closed to the fluid circuit. That is, bubble elimination port 16 is no longer in fluid communication with the fluid circuit. Specifically, it will be appreciated that, in the second position, barbs 22 of connector portion 20 form a fluid-tight annular seal with a second portion of first tube 10, upstream of bubble elimination port 16. In other words, bubble elimination port 16 is located distally of the annular seal, that is, closer to open end 14 of first tube 10. In this manner, the fluid circuit is free of any discontinuities that may tend to cause formation of thrombus.

The size and configuration of bubble elimination port 16 may vary depending on the particular application or procedure. In its simplest form, as shown in FIGS. 1 to 3, bubble elimination port 16 is merely a collection chamber formed by a convex protrusion in a sidewall of tube 10. The chamber of bubble elimination port 16 has a particular volume and communicates with the lumen 26 of tube 10, for collecting any bubbles that may form in the fluid circuit, e.g., during the first connecting stage or procedure. For example, in the embodiment of FIGS. 1 to 3, the volume may be in the range of about 0.5 to 2 cc., and preferably is about 1 cc. Those skilled in the art readily will be able to select the shape and volume of bubble elimination port 16 to suit any given application.

Figure 4:
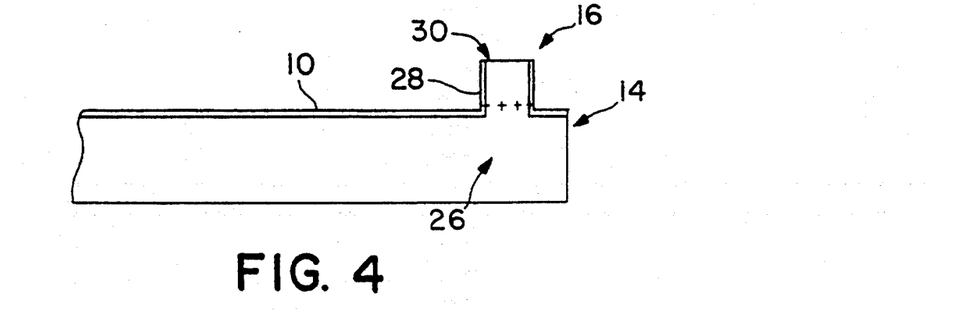
FIG. 4 is a side schematic view of an alternative embodiment of the bubble elimination port of the present invention, including a vent to the exterior environment.

In other embodiments, as shown in FIGS. 4 to 7, bubble elimination port 16 may include a chamber body 28 and a vent 30, for communicating with the external environment. In one simple form, as shown in FIG. 4, chamber body 28 is generally cylindrical or tubular, and vent 30 is formed by truncating a distal end thereof.

Figure 5:
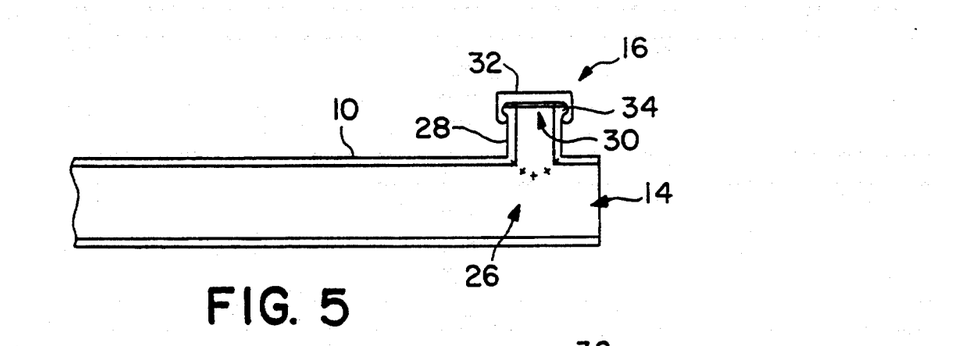
FIG. 5 is a side schematic view of another embodiment of the bubble elimination port of the present invention, including a removable cap.

Alternatively, as shown in FIG. 5, bubble elimination port 16 may be provided with a cap 32. Cap 32 may be removable but securely attachable to chamber body 28 by conventional means, such as a lip 34 formed at the open distal end thereof. It will be appreciated that removable cap 32 may facilitate the above-described procedure for using the system, either by venting bubble elimination port 16 during the priming stage (see FIG. 1), by subsequently venting bubble elimination port 16 during the first connecting stage (see FIG. 2), or both. It also will be appreciated that, for a particular application, in this embodiment the volume of bubble elimination port 16 may be significantly smaller than in the embodiment of FIGS. 1 to 3, because any bubbles entrapped in port 16 may be vented to the external environment to allow additional bubbles in the fluid circuit to be removed to port 16 and vented.

Figure 6:
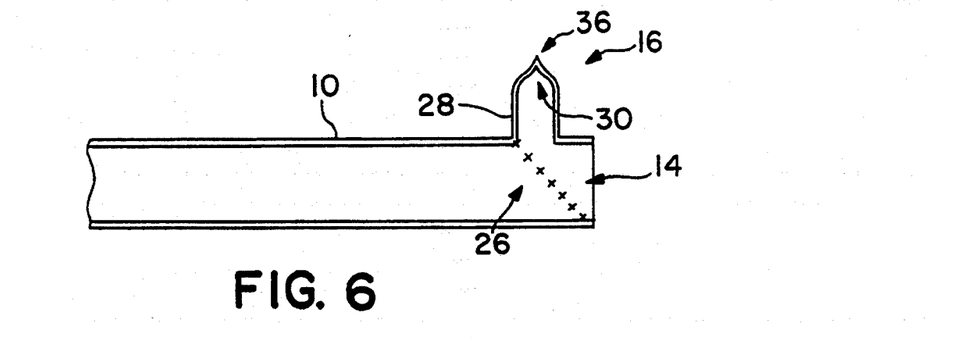
FIG. 6 is a side schematic view of another embodiment of the bubble elimination port of the present invention, including a one-way valve.

FIG. 6 illustrates another embodiment of bubble elimination port 16, wherein vent 30 comprises a one-way valve 36. In this configuration a clinician can be assured that no air or other environmental elements will be introduced to the fluid circuit through bubble elimination port 16 during either the priming stage or the connecting stages. In addition to allowing for a smaller sized bubble elimination port 16, this embodiment has particular utility where port 16 is formed of a flexible material, and can be vented merely by pinching or occluding chamber body 28. Moreover, it will be appreciated that repeated or successive venting of chamber body 28 through vent 30 thus can create a vacuum that will suck fluid and any further bubbles into chamber body 28 from the fluid circuit, in a manner similar to the "roll-up" procedure, to assure a bubble-free connection. One example of a one-way valve is a duck-bill valve, which is self-closing and, thus, facilitates easy operation by a single clinician.

Figure 7:
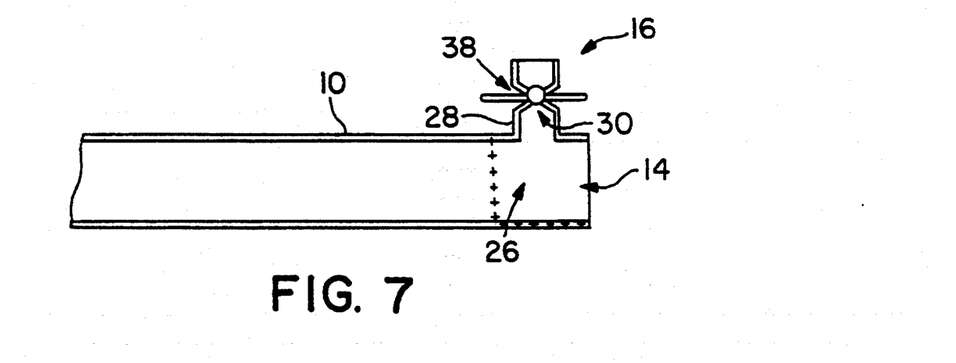
FIG. 7 is a side schematic view of another embodiment of the bubble elimination port of the present invention, including a two-way valve.

FIG. 7 illustrates yet another embodiment of bubble elimination port 16, wherein vent 30 comprises a two-way valve 38. For example, as shown in FIG. 7, two-way valve 38 may be a stop-cock. In this configuration, a clinician can vent to the external environment any bubbles collected in bubble elimination port 16 during either the priming stage or the first connecting stage. Also, during the first connecting stage two-way valve 38 may be utilized to introduce any desired fluids or medication prior to the final connecting stage where tubes 10,12 are connected in a continuous, fluid-tight circuit (see FIG. 3).

In each of the above embodiments, bubble elimination port 16 is formed as an integral portion of first tube 16, and remains a portion of the connected system. However, bubble elimination port 16 may be designed to be removable from the system after the final connecting stage is completed. For example, bubble elimination port 16 may be removed by cutting it off, for example, with a knife. Alternatively, an overlapping portion of first tube 10 may be provided with a score line, as variously shown in phantom in FIGS. 4 to 7, and bubble elimination port 16 may be removed by ripping or pulling it free of first tube 10. In this manner, bubble elimination port 16 selectively may be removed during procedure. Moreover, although only the protruding portion need be removed to prevent accidental or inadvertent catching of the port during procedure, it will be appreciated that removal of the entire overlapping portion of first tube 10, that is, the portion distal of the annular seal formed with barbs 22, will facilitate viewing of the continuous fluid channel to assure a bubble-free connection.

Figure 8:
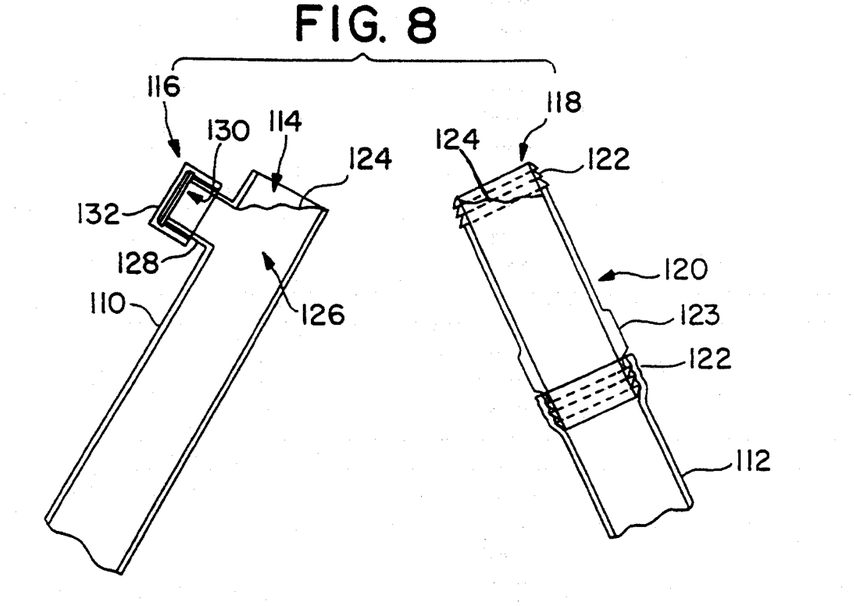
FIG. 8 is a side schematic view of a second embodiment of a connector system of the present invention including a connector tube.
Figure 9:
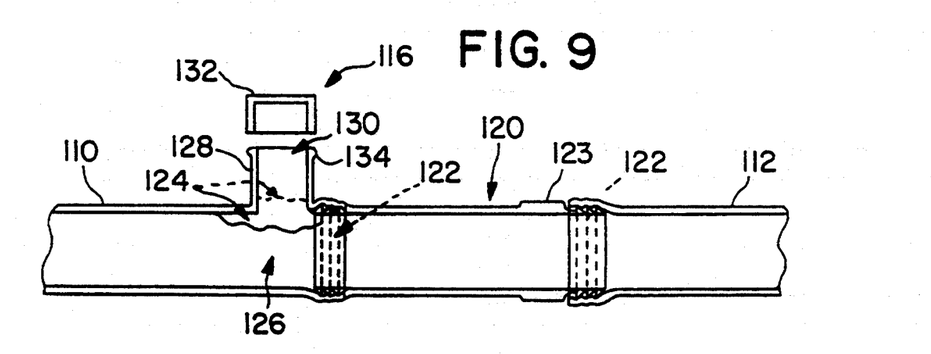
FIG. 9 is a side schematic view of the connector system of FIG. 8, wherein the connector tube is inserted to a first position, and a bubble elimination port of the first tube is open to a fluid-tight circuit.
Figure 10:
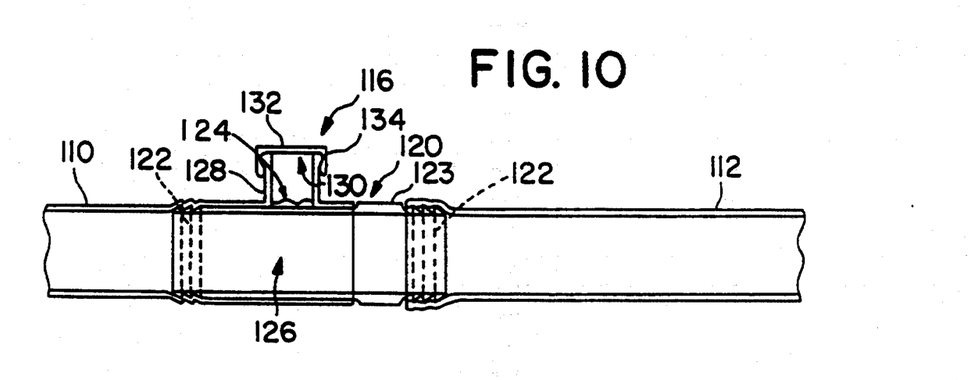
FIG. 10 is a side view of the connector system of FIG. 8, wherein the connector tube is inserted to a second position, and a bubble elimination port of the first tube is closed to a continuous, fluid-tight circuit.

FIGS. 8 to 10 illustrate a second embodiment of a bubble-free connector system of the present invention. In this embodiment, the system includes a first tube 110, a second tube 112, and a connector tube 120. As in the previous embodiment, first tube 110 has an open end 114 and a bubble elimination port 116 disposed proximate open end 114, and axially displaced therefrom. Second tube 112 has an open end 118.

The size, composition and arrangement of tube 110, open end 114 and bubble elimination portion 116 are the same as the corresponding elements in the embodiment of FIGS. 1 to 3, except that port 116 includes a vent 130 and cap 132 arrangement as shown in FIG. 5. Of course, one skilled in the art readily will appreciate that these characteristics may be varied and modified to accommodate numerous applications.

The size, composition and arrangement of second tube 112 also may be varied and modified to accommodate numerous applications. However, in order to provide a smooth, continuous fluid flow, the sizing and composition of second tube 112 generally will be the same as, or comparable to, that of first tube 110.

Connector tube 120 is sized and configured to be inserted into tubes 110,112 to provide a continuous fluid channel or circuit. In the present embodiment, connector tube 120 is a ⅜ inch inner diameter—9/16 inch outer diameter tube, and is about 3 inches long. Connector tube 120 may include one or more annular ridges or barbs 122 proximate each end thereof for providing a secure but removable connection between such ends and open ends 114,118 of first and second tubes 110,112. For example, as shown in FIGS. 8 to 10, connector tube 120 may have 2 sets of 3 barbs located in respective ¼ inch long portions adjacent each end thereof. As in the previous embodiment, it will be appreciated that annular barbs 122 will form an annular, fluid-tight seal with the respective inner walls of first and second tubes 110,112. Connector tube 120 also may include an annular grip 123 to facilitate manipulation by a clinician. Finally, connector tube 120 preferable is composed of a clear, rigid material suitable for carrying blood, and most preferably is composed of polypropylene, to facilitate viewing by the clinician during the bubble elimination stage.

The method for using the system of FIGS. 8 to 10 is substantially similar to that of the embodiment of FIGS. 1 to 3. Specifically, in the present embodiment, one end of connector tube 120 first is inserted into open end 118 of second tube 112. In this manner, as shown in FIG. 8 (priming stage), connector tube 120 forms an extension of second tube 112, including a connector portion (connector tube 120) for effecting a fluid-tight connection between first tube 110 and second tube 112. Thus, it will be appreciated that this embodiment has particular utility in applications where tube 112 is a standard tubing.

Referring now to FIG. 9, in a first connecting stage the open end of connector tube 120 is inserted into open end 114 of first tube 110 to form an annular, fluid-tight seal between barbs 122 of connector tube 120 and first tube 110 at open end 114. As in the previous embodiment, in the first position, bubble elimination port 116 is open to a closed, fluid-tight channel or circuit. As shown therein, during this connecting stage, a bubble may be formed in the fluid circuit. However, any bubble may be removed from the fluid circuit to bubble elimination port 116 by a well known method, such as by tapping the tubing.

In a case where the volume of a bubble is greater than the volume of bubble elimination port 116, as shown in FIG. 9, cap 132 may be removed to allow the bubble to escape to the external environment. In this manner, any bubble in the fluid circuit may be removed. Moreover, as a bubble is removed to the external environment, a small amount of fluid from the fluid circuit may be biased into bubble elimination port 116, as shown by dotted lines in FIG. 9, by conventional means, such as a roll-up technique, or by pinching second tube 112, to insure that the fluid channel or circuit is bubble-free.

Referring now to FIG. 10, in a second or final stage connector tube 120 is further inserted into the first tube 110 to a second position, to form an annular, fluid-tight seal upstream of bubble elimination port 116. As shown therein, bubble elimination port 116 is closed to a continuous, fluid-tight channel or circuit, that is, without forming any discontinuities in the fluid circuit that may tend to cause thrombus.

Figure 11:
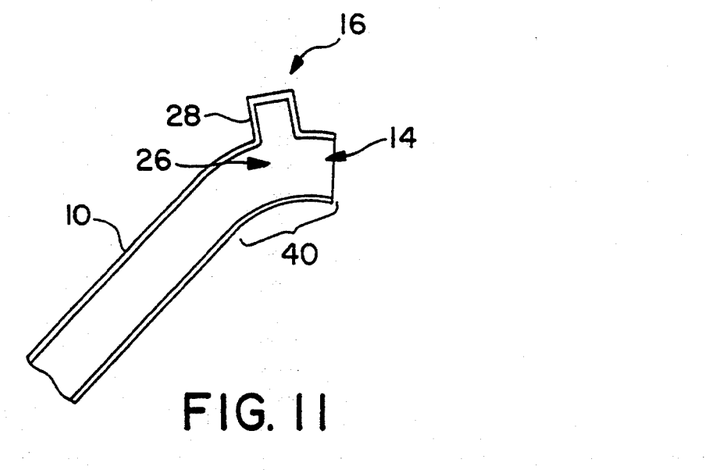
FIG. 11 is a side schematic view of an alternative embodiment of a first tube of the connector system of the present invention having a curved portion formed proximate an open end thereof, and including a bubble elimination port located on the curved portion.

FIG. 11 illustrates an alternative embodiment of a first tube 10 of the present invention. In this embodiment, first tube 10 is composed of a flexible material, such as PVC or the like, and has a curved portion 40 proximate open end 14. Bubble elimination port 16 is located on curved portion 40, preferably at a high point thereof. In this manner, it will be appreciated that any bubbles in the fluid circuit, including bubbles formed during either the priming stage or the connecting stage, inherently will tend to rise to the high point, and into bubble elimination port 16. Thus, bubble elimination is facilitated. Moreover, since first tube 10 is formed of a flexible material, it will be appreciated that, as the connector portion or tube is inserted into first tube 10 to the second position, it will cause curved portion 40 to conform to the configuration thereof, e.g., to straighten out. In this manner, the connector portion or tube is less likely to become accidentally disconnected from tube 10 during procedure. In order to further facilitate insertion, a portion of first tube 10 proximate open end 14 may be pretreated. For example, the curved portion may be prestretched. Alternatively, first tube 10 may be formed of a heat sensitive material, and the portion proximate open end 14 can be preheated to soften it.

Figure 12:
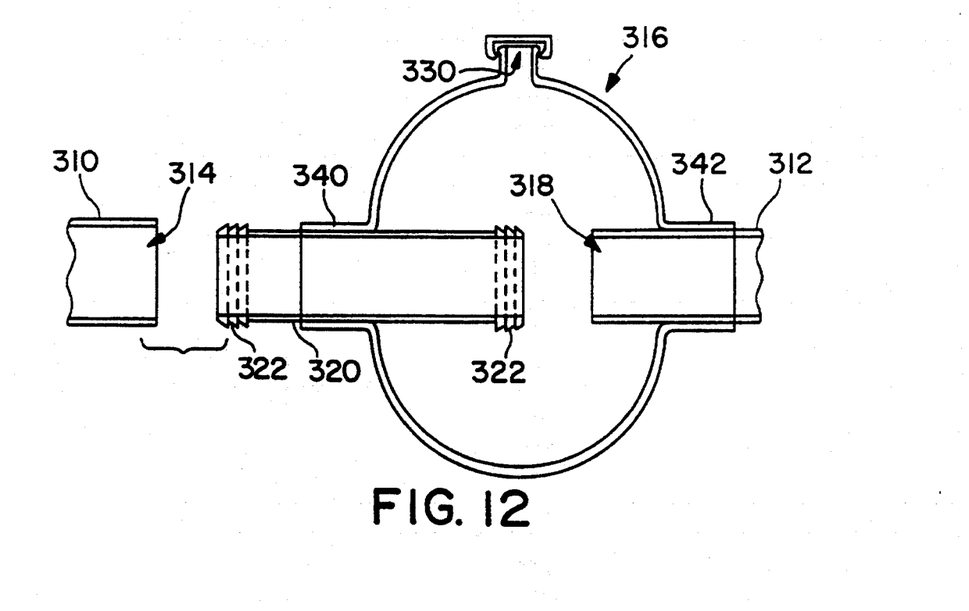
FIG. 12 is a side schematic view of a third embodiment of a connector system of the present invention including a connector tube and balloon system.

FIG. 12 illustrates in side schematic view a third embodiment of a connector system of the present invention. In this embodiment, the system generally includes a first tube 310, a second tube 312 and means for connecting tubes 310,312 in a continuous, bubble-free fluid circuit. Specifically, in the embodiment of FIG. 12, the connecting means includes a bubble elimination balloon 316 and a connector tube 320.

The size, composition and configuration of first tube 310, second tube 312 and connector tube 320 generally is the same as that in the embodiment of FIGS. 8 to 10, except that first tube 310 is not provided with a bubble elimination port. Rather, the system is provided with a bubble elimination balloon 316. Balloon 316 is provided with a first connecting port 340 for connecting to connector tube 320, and a second connecting port 342 for connecting to first tube 310. Specifically, each connecting port 340,342 may be a stretchable annular or tubular opening which forms a fluid-tight seal, respectively, with connector tube 320 and first tube 310. For example, in the embodiment of FIG. 12, balloon 316 is composed of a latex material.

In one method for using the system of FIG. 12, connecting ports 340,342 are connected, respectively, to one end of connector tube 320 and open end 314 of first tube 310, as shown in FIG. 12. The subsequent stages of the present connecting procedure are similar to the above-described procedures. The open end of connector tube 320 is inserted into second tube 312 to form an extension or connector portion thereof. Upon this connection, it will be appreciated that tubes 310,312 connector 320 and balloon 316 form a fluid-tight circuit. Thus, at this time the priming stage can be carried out without worry of any prime fluid spilling from the circuit. Specifically, in the priming stage of the present embodiment, prime fluid is introduced through one or both of tubes 310,312 until balloon 316 is filled sufficiently that open end 314 of first tube 310 and the free open end of connector tube 320 are submerged in prime fluid 324, and any bubbles formed therein are removed to bubble elimination balloon 316. During this stage, bubble elimination balloon 316 may be drained or deflated through a vent 330, such as a luer valve, etc., so that balloon 316 does not become overstretched. Then, the open end of connector tube 320 may be inserted into open end 314 of first tube 310 to form a continuous, bubble-free fluid channel or circuit. Thereafter, bubble elimination balloon 316 may be drained through vent 330 so that bubble elimination balloon 316 does not create a significant protrusion. Alternatively, balloon 316 may be cut or torn away, to eliminate any protrusion from the fluid circuit.

FIGS. 13 to 16 illustrate in side schematic view still another embodiment of a connector system of the present invention. In this embodiment, the system generally includes a first tube 410, a tube fitting 412 and means for connecting the tube 410 and the tube fitting 412 in a continuous, fluid-tight bubble-free, circuit. Specifically, in the embodiment of FIGS. 13 to 16, the connecting means includes a generally tubular soft connector 420 having a bubble elimination chamber 416.

The sizing, composition and configuration of first tube 410 generally is the same as that in the embodiment of FIG. 12, that is, a standard flexible tube.

Figure 14:
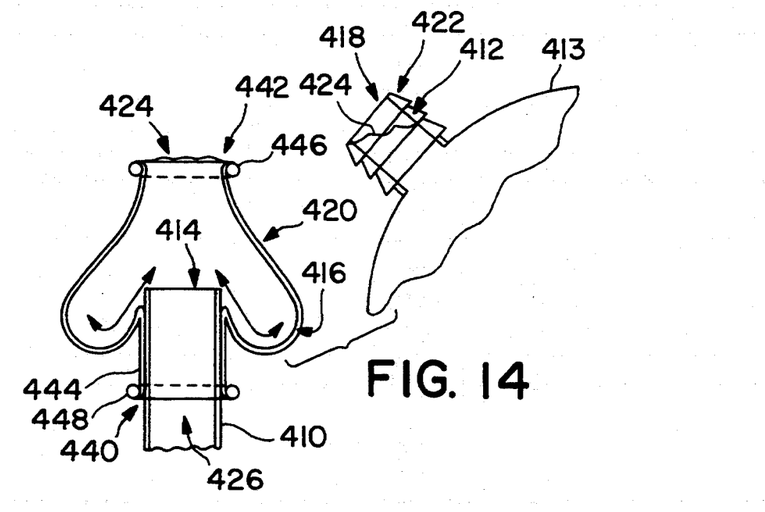
FIG. 14 is a side schematic view of a connector system of the present invention using the connector of FIG. 13.

Tube fitting 412 may be a port fitting of a second tube, a connector tube, or another element of a fluid circuit. For example, tube fitting 412 may be a rigid connector tube as shown in the embodiments of FIGS. 8 to 10 or FIG. 12. Alternatively, as shown in FIG. 14, tube fitting 412 may be a barbed port fitting of a pump housing 413. Thus, it will be appreciated that this embodiment may be adapted to any application having a tube fitting 412, and is not limited to applications wherein there is a second tube having an annular or cylindrical connector portion, although it includes those applications as well. In other words, although the present embodiment may be used in an application for connecting two tubes, it is not limited thereto. As discussed in greater detail below, the configuration of tube fitting 412 in this embodiment is limited only to the extent that tube fitting 412 must be capable of forming a fluid tight seal with each of (first) tube 410 and connector sleeve 420.

Figure 13:
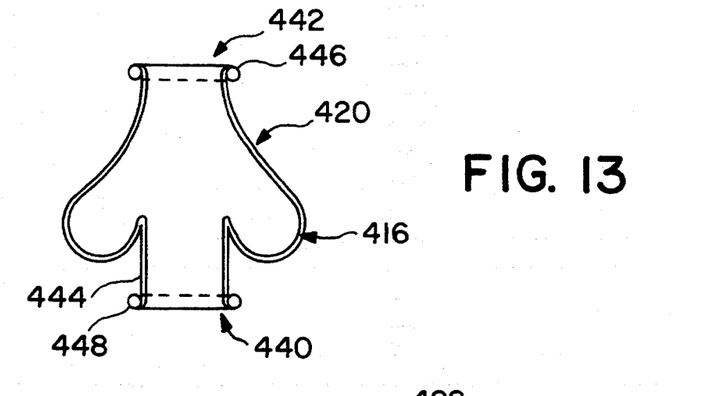
FIG. 13 is a side schematic view of yet another embodiment of the present invention, including a soft connector having a connecting sleeve and a coaxial bubble elimination chamber.

Referring now to FIG. 13, in one embodiment connector 420 includes a first connecting port 440, a second connecting port 442, a bubble elimination chamber 416, and a sleeve portion 444. As shown in this embodiment, bubble elimination chamber 416 of connector 420 is bulbous, and in longitudinal cross-section is generally heart-shaped. Specifically, bubble elimination chamber 416 is truncated at the tapered end of the heart-shape to form second connecting port 442. The other end of bubble elimination chamber 416 is arranged generally coaxially with and in fluid communication with the lumen of sleeve portion 444 and with sleeve connecting port 440. In this manner, bubble elimination chamber 416 is disposed proximate to second connecting port 442 and axial displaced therefrom.

As shown in FIGS. 13 to 16, connecting ports 440, 442 may include respective lips 448, 446 at the ends thereof. As discussed in greater detail below, lips 446, 448 may function as finger grips for facilitating manual manipulation during the connecting steps. Lips 446, 448 also may provide a biasing or reinforcing force, such that a flexible, reliable, fluid-tight annular seal is provided with first tube 410 and tube fitting 412. Connector 420 may be composed of any flexible material suitable for handling blood, and preferably is formed of latex or silicon.

By way of example, in the embodiment of FIGS. 13 to 16, soft connector 420 is composed of a soft flexible material suitable for medical applications (blood compatible), such as latex, silicon or the like, and has a 1/16 inch material thickness. Sleeve 444 is ⅜ inches long with a 9/16 inch i.d., bubble elimination chamber 416 is about 1¼ inches long with a maximum diameter of about 1¼ inches, and second connecting port 442 is about ⅜ inches i.d. Bubble elimination chamber 416 preferably has a volume in the range of about 0.5 to 4 cc, and most preferably in the range of about 1 to 2 cc. Of course, those skilled in the art readily will be able to vary and select the composition and dimensions of soft connector 420 in accordance with a desired application.

Referring now to FIG. 14, in a preferred method of using the soft connector 420 of the present embodiment, the open end 414 of tube 410 is inserted into first connecting port 440 of connector 420 and through sleeve 444. It will be appreciated that this insertion is facilitated by holding the lip 448 of connector 420 between the fingers of one hand while manipulating first tube 410 with the other hand. As shown in FIG. 14, tube 410 preferably is inserted completely through sleeve 444 so that open end 414 thereof extends slightly into bubble elimination chamber 416. In this manner, connector 420 becomes an extension of tube 410 and bubble elimination chamber 416 is in fluid communication with the lumen 426 of tube 410.

The assembly consisting of tube 410 and connector 420 (first tube assembly) then is oriented generally vertically with second connecting port 442 elevated, and the first tube assembly is primed with a prime fluid 424 by any conventional method. Referring particularly to FIG. 14, it will be appreciated that the inverted heart shape of connector 420 facilitates a continuous flow of prime fluid 424 within bubble elimination chamber 416, as shown by arrows therein, to quickly and reliably eliminate any bubbles formed on the walls in tube 410 and connector 420 during the priming stage. Tube fitting 412 likewise is preferably oriented in an elevated position, and is primed by a conventional method, as shown in FIG. 14.

Figure 15:
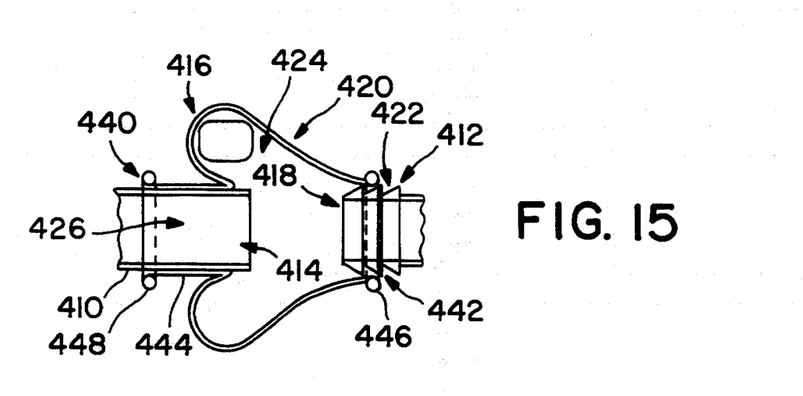
FIG. 15 is a side schematic view of the system of FIG. 14, wherein a tube, the connector, and a barb fitting are connected in a first position and the bubble elimination chamber is open to a fluid-tight circuit.

Referring now to FIG. 15, in a first connecting stage the open end 418 of tube fitting 412 is inserted into the second connecting port 442 of connector 420 to a first position, so that lip 446 rides up on barbs 422 of tube fitting 412. As shown therein, tube fitting 412 preferably has a plurality of annular ribs or barbs 422, and lip 446 rides up on at least one of barbs 422 to form a fluid-tight annular seal between connector 420 and tube fitting 412. In this manner, it will be appreciated that tube 410, connector 420 and tube fitting 412 form a fluid-tight circuit, and bubble elimination chamber 416 is in fluid communication with that circuit.

As in the prior embodiments, any bubbles trapped or located in the circuit then may be moved from the circuit to bubble elimination chamber 416 by manipulating the circuit, e.g., by tapping the circuit elements, as is known in the art. As shown in FIG. 15, any air bubbles so moved naturally will rise into the bulbous portion of bubble chamber 416, well clear of a primary circuit path formed by tube 410 and tube fitting 412.

Figure 16A:
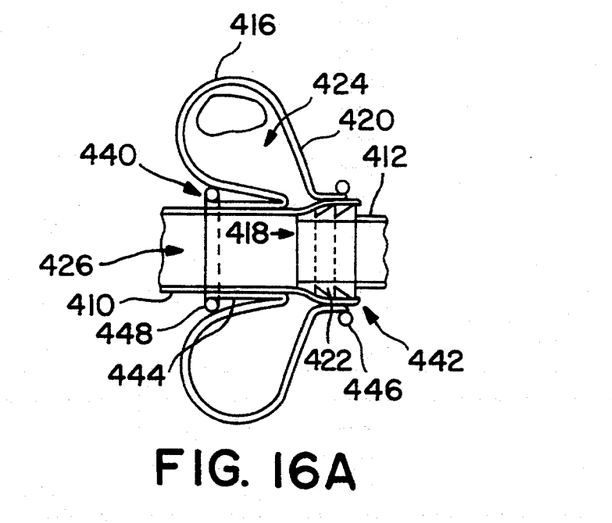
FIGS. 16A and 16B are side schematic views of the system of FIG. 14, wherein a tube, the connector, and a barb fitting are connected in a second position, and the bubble elimination chamber is closed to a continuous, fluid-tight circuit.
Figure 16B:
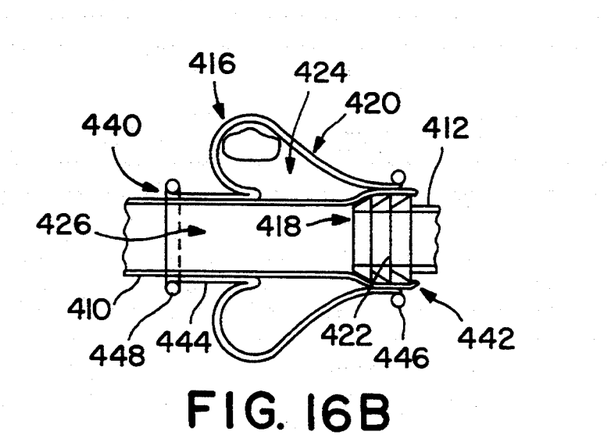

Referring now to FIG. 16A, in a second or final connecting stage, tube 410 is advanced through bubble elimination chamber 416 to a second position, wherein the open end 418 of tube fitting 412 is inserted into the open end 414 of tube 410. In so doing, it will be appreciated that tube 410 will be inserted into an annular nip formed between the barbs 422 of tube fitting 412 and the end of the heart-shaped bubble elimination chamber 416, i.e., connecting port 442, so that, as tube 410 continues to advance over barbs 422 of tube fitting 412, it will also advance under flexible lip 446 of connector 420. In other words, in this procedure both tube 410 and connector 420 preferably are advanced over barbs 422, thereby to form a secure, fluid-tight seal. At the same time, it will be appreciated that the flexible heart-shaped configuration of connector 420 allows the bulbous bubble elimination chamber 416 to roll back over the sleeve portion 444 of connector 420, while maintaining a fluid-tight seal between sleeve 444 and tube 410. Alternatively, or in addition, sleeve 444 may be pulled back over tube 410, as shown in FIG. 16B. Of course, this procedure is greatly facilitated by manually manipulating lip 448.

As in previous embodiments, upon final connection of tube 410 and tube fitting 412, connector 420 may be removed, e.g., by cutting it away with a knife. Alternatively, connector 420 may be provided with score lines, and it may be torn away.

Figure 17:
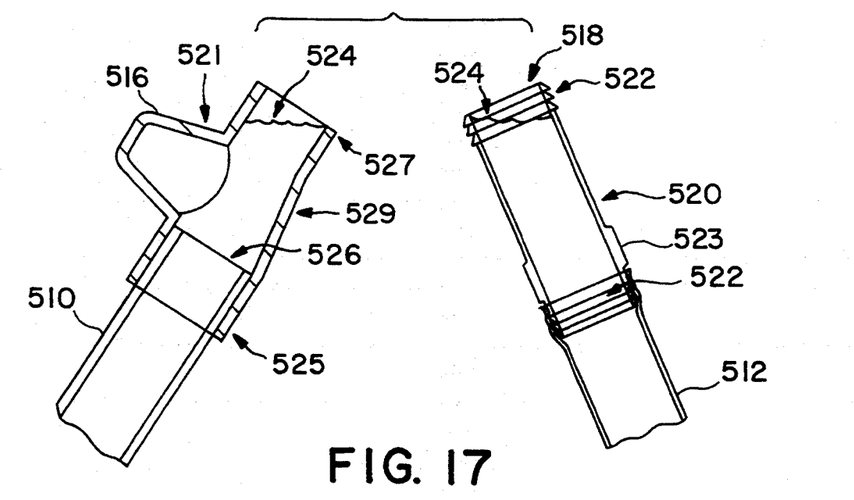
FIG. 17 is a side schematic view of a further embodiment of the present invention including a first tube assembly of a first tube and a soft connector, and a second tube assembly of a second tube and a rigid connector tube.
Figure 18:
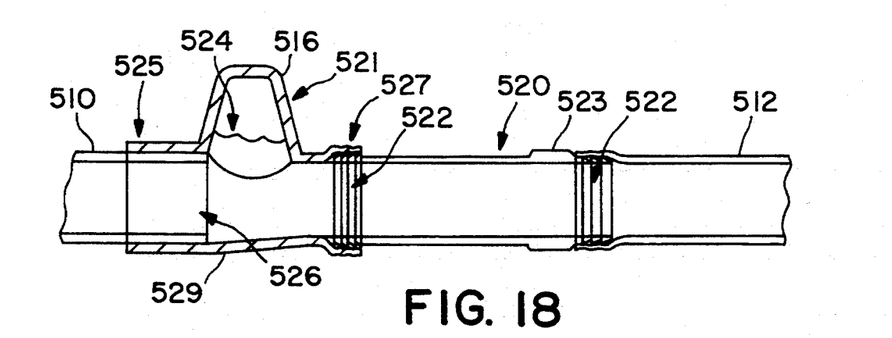
FIG. 18 is a side schematic view of the system of FIG. 17, wherein the first and second tube assemblies are connected in a first position, and the bubble elimination chamber is open to a fluid circuit.
Figure 19:
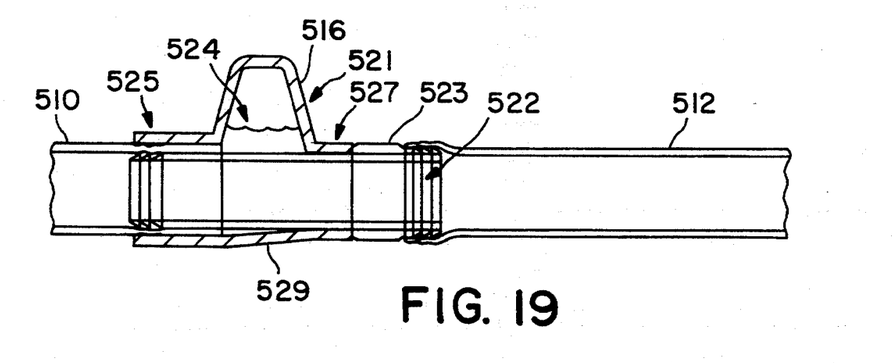
FIG. 19 is a side schematic view of the system of FIG. 17, wherein the first tube, the second tube and the connector tube are connected in a second position, and the bubble elimination chamber is closed to a continuous, fluid-tight circuit.

FIGS. 17 to 19 illustrate in schematic view yet another embodiment of a connector system of the present invention including a soft connector. In this embodiment, the system generally includes a first tube 510, a second tube 512, a connector tube 520 and a soft connector 521. As discussed in greater detail below, soft connector 521 and connector tube 520 constitute means for connecting first tube 510 and second tube in a continuous, fluid-tight, bubble-free circuit.

Soft connector 521 is generally tubular, and includes a first connecting port 525, a second connecting port 527, and a bubble elimination chamber 516. Bubble elimination chamber 516 is located between first connecting port 525 and second connecting port 527 and is in fluid communication with the lumen of soft connector 521. As best shown in FIG. 17, the diameter of first connecting port 525 preferably is larger than the diameter of second connecting port 527, and the soft connector 521 has a tapered portion 529 between first connecting port 525 and second connecting port 527. As discussed in greater detail below, this configuration facilitates connection of the various system elements.

In a preferred embodiment, as shown in FIGS. 17 to 19, bubble elimination chamber 516 is located on tapered portion 529. More specifically, bubble elimination chamber 516 preferably has a closed, truncated conical configuration with an open end having a length substantially equal to the axial length of the tapered portion 529, and a width substantially equal to the cross-sectional diameter of connector 520 at a midpoint along the axial length of tapered portion 529. It will be appreciated that this configuration will minimize any discontinuities in the fluid circuit between bubble elimination chamber 516 and the lumen of soft connector 520, and thereby facilitate continuous fluid communication therebetween.

By way of example, in the embodiment of FIGS. 17 to 19, soft connector 520 is composed of a soft, flexible material suitable for medical applications (blood compatible), such as latex, silicon or the like, and has a 0.06 inch material thickness. First connecting port 525 is 0.50 inch long by 0.563 inch i.d.; second connecting port 527 is 0.50 inch long by 0.430 inch i.d. Tapered portion 529 is 0.50 inch long with an 8° taper. Bubble elimination chamber 516 is 0.44 inch high by 0.40 inch i.d. at the open end and 0.24 inch i.d. at the closed, truncated end. Bubble elimination chamber 516 preferably has a volume in the range of about 0.5 to 4 cc, and most preferably in the range of about 1 to 2 cc. Of course, those skilled in the art readily will be able to vary and select the composition and dimensions of the soft connector 520 in accordance with a desired application.

The sizing, composition and configuration of first tube 510, second tube 512, and connector tube 520 generally is the same as the embodiment of FIGS. 8 to 10. That is, first tube 510 and second tube 512 are standard flexible tubing, and connector tube 520 is a rigid tube as shown in FIGS. 8 to 10.

A preferred method for using the soft connector system of FIGS. 17 to 19 is substantially similar to the above-described method for the embodiment of FIGS. 8 to 10. Initially, the open end of first tube 510 is inserted into first connecting port 525, such that connector 520 becomes an extension of tube 510 (hereinafter "first tube assembly"), and bubble elimination chamber 516 is in fluid communication with the lumen 526 of tube 510. Specifically, when the open end of the first tube is inserted into first connecting port 525 of soft connector 521, a fluid-tight annular connection is formed therebetween, bubble elimination chamber 516 is located proximate to and axially displaced from the open end of the first tube assembly, i.e., second connecting port 527, and bubble elimination chamber 516 is in fluid communication with the lumen of first tube 510.

Likewise, one end of connector tube 520 is inserted into the open end of second tube 512, such that connector tube 520 becomes an extension of second tube 512 (hereinafter "second tube assembly"). Specifically, when the first open end of the connector tube is inserted into the open end of the second tube, a fluid-tight annular connection is formed therebetween, and connector tube 520 functions as a connecting portion of the second tube assembly.

The first tube assembly then is oriented generally vertically, with second connecting port 527 elevated, and is primed with a prime fluid 524. Likewise, the second tube assembly is oriented generally vertically, with the open end of connector tube 520 elevated, and is primed with prime fluid 524.

In a first connecting stage, as shown in FIG. 18, the other or second end (open end) of connector tube 520 is inserted into the second connecting port 527 of soft connector tube 521 to a first position, where first tube 510, soft connector 521, connector tube 520 and second tube 512 form a continuous fluid channel or circuit. In this configuration, second connecting port 527 forms a fluid-tight annular seal with barbs 522 of the second end of connector tube 520, and bubble elimination chamber 516 is open to lumen 526 of first tube 510. That is, bubble elimination chamber 516 is in fluid communication with the continuous fluid circuit to permit removal of any bubbles formed in the fluid circuit to bubble elimination chamber 516.

In a second connecting stage, as shown in FIG. 19, connector tube 520 further is inserted into soft connector 521 to a second position, where the second end of connector tube 520 forms a fluid-tight annular seal with first tube 510 downstream of bubble elimination chamber 516. In this configuration, first tube 510, connector tube 520 and second tube 512 form a continuous, fluid-tight, bubble-free fluid circuit, and bubble elimination chamber 516 is closed to the circuit by connector tube 520.

In another aspect, the method of the present invention may be modified such that bubble elimination chamber 516 is utilized to reduce or eliminate bubble formation during the first connecting stage. Specifically, in this aspect the respective first and second tube assemblies first are inclined and primed. Then, in the first connecting stage, as the first and second tube assemblies are being connected in the first position, the clinician gradually pinches the soft bubble elimination chamber to provide a flow of prime fluid 524 to the connection site. In this manner a "roll-up" type priming operation is performed during the first connecting stage, to reduce or prevent formation of any bubbles in the fluid circuit.

In a further aspect, this method may be modified such that bubble elimination chamber 516 also is utilized to facilitate bubble elimination after the first connecting stage. Specifically, at the end of the first connecting stage, the clinical may release the pinched bubble elimination chamber 516, which then will tend to reinflate due to the elastic memory of the flexible tubing. In this manner, priming fluid and any bubbles that may be present at the connection site will be drawn to bubble elimination chamber 516. That is, bubble elimination chamber 516 functions as a vacuum chamber for facilitating removal of any bubbles in the fluid circuit.

In the embodiment of FIGS. 17 to 19, a second tube assembly including second tube 512 and connector tube 520 is disclosed. However, connector 521 also has utility for connecting a first tube and a tube fitting, as illustrated in the embodiment of FIGS. 13 to 16.

Although the present invention has been described with respect to several specific embodiments and applications, it is not limited thereto. Numerous variations and modifications readily will be appreciated by those skilled in the art and are intended to be included within the scope of the present invention, which is recited in the following claims.

What we claim is:

1. A connector system for a liquid carrying circuit, the system comprising:
   a tube having a lumen therethrough and an open end;
   a tube fitting having a lumen therethrough and an open end; and
   connector means, including a generally tubular soft connector having an axis and lumen therethrough from a first connecting port to a second connecting port, and a bubble elimination chamber formed by a wall of said connector means proximate to and axially displaced from the second connecting port and in fluid communication with the lumen of said connector means, for connecting said tube and said tube fitting in a first position, with the open end of the tube fitting and the first connecting port forming a fluid-tight connection, the lumen of said tube, the lumen of said soft connector, and the lumen of said tube fitting forming a continuous fluid circuit and the bubble elimination port being open to the fluid circuit, and for connecting said tube and tube fitting in a second position, the lumen of said tube and the lumen of said tube fitting forming a continuous, fluid-tight circuit and the bubble elimination port being closed to the circuit by the tube fitting.

2. The system of claim 1, wherein said soft connector comprises a sleeve portion, and wherein said bubble elimination chamber is arranged coaxially with said sleeve portion.

3. The system of claim 2, wherein said bubble elimination chamber is generally heart-shaped in longitudinal cross-section.

4. The system of claim 3, wherein a tapered portion of the heart-shaped bubble elimination chamber is truncated to form said second connecting port.

5. The system of claim 1, wherein at least one of said first and second connecting ports comprises an annular lip for facilitating manual manipulation of said connector means.

6. The system of claim 5, wherein each of said first and second connecting ports comprises an annular lip.

7. The system of claim 2, wherein said bubble elimination chamber has a volume in a range of about 0.5 to 4 cc.

8. The system of claim 2, wherein said bubble elimination chamber has a volume in a range of about 1 to 2 cc.

9. The system of claim 1, wherein said tube fitting comprises at least one annular ridge proximate the open end of said tube fitting.

10. The system of claim 9, wherein said tube fitting comprises three annular ridges proximate the open end of said tube fitting.

11. The system of claim 1, wherein the first connecting port has a first diameter, the second connecting port has a second diameter smaller than the first diameter, and the soft connector has a tapered portion located between the first connecting port and the second connecting port.

12. The system of claim 11, wherein the bubble elimination chamber is located on the tapered portion of said soft connector.

13. The system of claim 12, wherein the bubble elimination chamber has an opening in fluid communication with the lumen of the soft connector, the opening having a length substantially equal to an axial length of the tapered portion and a width substantially equal to a diameter of the soft connector at a midpoint of the axial length of the tapered portion.

14. The system of claim 1, wherein the bubble elimination chamber has a generally conical configuration.

15. The system of claim 11, wherein the bubble elimination chamber has a generally conical configuration.

16. The system of claim 12, wherein the bubble elimination chamber has a generally conical configuration.

17. The system of claim 13, wherein the bubble elimination chamber has a generally conical configuration.

18. The system of claim 14, wherein the bubble elimination chamber has a volume in the range of about 0.5 to 4 cc.

19. The system of claim 14, wherein the bubble elimination chamber has a volume in the range of about 1 to 2 cc.

20. The system of claim 1, further comprising a second tube having a lumen therethrough and an open end, and wherein said tube fitting is a connector tube having a second open end in fluid communication with the lumen of the connector tube, for connecting to said second tube, to form an extension thereof.

21. The system of claim 20, wherein said second tube is a flexible tube and said connector tube is sized for insertion into the open end of said second tube for forming a fluid-tight annular seal with said second tube.

22. The system of claim 21, wherein the second open end of said connector tube comprises at least one annular barb.

23. The system of claim 22, wherein the second open end of said connector tube comprises three annular barbs.

24. A method for connecting a liquid carrying circuit, the circuit including a first tube having a lumen therethrough and an open end, a tube fitting having a lumen therethrough and an open end, and a soft connector having a lumen therethrough from a first connecting port to a second connecting port and a bubble elimination chamber in fluid communication with the lumen thereof, the method comprising the steps of:
   connecting the open end of the first tube to the first connecting port of the soft connector to form a fluid-tight connection therebetween, thereby to form a first tube assembly;
   priming each of the first tube assembly and the tube fitting with priming fluid;

connecting the first assembly and tube fitting in a first position, to form a fluid-tight connection between the open end of the tube fitting and the second connecting port, and to form a continuous fluid circuit including the lumen of the first tube, the lumen of the soft connector and the lumen of the tube fitting, the bubble elimination chamber being open to the fluid circuit; and connecting the first tube assembly and the tube fitting in a second position, to form a continuous, fluid-tight circuit including the lumen of the first tube and the lumen of the tube fitting, the bubble elimination chamber being closed to the fluid-tight circuit by the tube fitting.

25. The method of claim 24, further comprising the step of eliminating any bubbles in the fluid circuit by moving the bubbles from the fluid circuit to the bubble elimination chamber after the step of connecting the first tube assembly and the tube fitting in the first position and prior to the step of connecting the first tube assembly and the tube fitting in the second position.

26. The method of claim 24, further comprising the step of pinching the bubble elimination chamber during the step of connecting the first tube assembly and the tube fitting in a first position, to provide a flow of prime fluid to a point of connection between the second connecting port and the open end of the tube fitting, thereby to reduce formation of any bubbles in the fluid circuit at the point of connection.

27. The method of claim 26, further comprising the step of releasing the pinched bubble elimination chamber after the step of connecting the first tube assembly and the tube fitting in the first position, to facilitate removal of any bubbles in the fluid-circuit by vacuum.

28. The method of claim 24, further comprising the step of removing the soft connector from the liquid carrying circuit after the step of connecting the first tube assembly and the tube fitting in the second position.

29. A method for connecting a liquid carrying circuit, the circuit including a first tube having a lumen therethrough and an open end, a soft connector having a lumen therethrough from a first connecting port to a second connecting port and a bubble elimination chamber in a fluid communication with the lumen thereof, a connector tube having a lumen therethrough from a first open end to a second open end, and a second tube having a lumen therethrough and an open end, the method comprising the steps of:

connecting the open end of the first tube to the first connecting port of the soft connector, to form a fluid-tight connection therebetween, thereby to form a first tube assembly;

connecting the open end of the second tube to the first open end of the connector tube, to form a fluid-tight connection therebetween, thereby to form a second tube assembly;

priming each of the first and second tube assemblies with a priming fluid;

connecting the first tube assembly and the second tube assembly in a full position, to form a fluid-tight connection between the second open end of the connector tube and the second connecting port of the soft connector, and to form a continuous fluid circuit including the lumen of the first tube, the lumen of the soft connector, the lumen of the connector tube and the lumen of the second tube, the bubble elimination chamber being open to the fluid circuit; and connecting the first tube assembly and the second tube assembly in a second position, to form a continuous fluid-tight circuit including the lumen of the first tube, the lumen of the connector tube and the lumen of the second tube, the bubble elimination chamber being closed to the fluid-tight circuit by the connector tube.

30. The method of claim 29, further comprising the step of eliminating any bubbles in the fluid circuit by moving the bubbles from the fluid circuit to the bubble elimination chamber after the step of connecting the first tube assembly and the second tube assembly fitting in the first position and prior to the step of connecting the first tube assembly and the second tube assembly in the second position.

31. The method of claim 29, further comprising the step of pinching the bubble elimination chamber during the step of connecting the first tube assembly and the second tube assembly in a first position, to provide a flow of prime fluid to a point of connection between the second connecting port and the second open end of the connector tube, to reduce formation of any bubbles in the fluid circuit at the point of connection.

32. The method of claim 31, further comprising the step of releasing the pinched bubble elimination chamber after the step of connecting the first tube assembly and the second tube assembly in the first position, to facilitate removal of any bubbles in the fluid-circuit by vacuum.

33. The method of claim 29, further comprising the step of removing the soft connector from the liquid carrying circuit after the step of connecting the first tube assembly and the second tube assembly in the second position.

* * * * *

UNITED STATES PATENT AND TRADEMARK OFFICE
CERTIFICATE OF CORRECTION

PATENT NO. : 5,439,448  
DATED : August 8, 1995  
INVENTOR(S) : BORIS LESCHINSKY ET AL.

It is certified that error appears in the above-identified patent and that said Letters Patent is hereby corrected as shown below:

On the title page,

Insert: --Notice: The portion of the term of this patent and subsequent to the expiration of U.S. Patent No. 5,312,352 has been disclaimed.--

COLUMN 5

Line 58, "EMBODIMENT" should read --EMBODIMENTS--.

COLUMN 6

Line 7, "Tygon TM" should read --Tygon™--;  
Line 36, "Of" should read --Of--;  
Line 37, "tube 16" should read --tube 10--; and  
Line 39, "tube 16." should read --tube 10.--

COLUMN 8

Line 21, "16," should read --10,--.

COLUMN 9

Line 11, "preferable" should read --preferably--.

COLUMN 11

Line 43, "axial" should read --axially--.

UNITED STATES PATENT AND TRADEMARK OFFICE
CERTIFICATE OF CORRECTION

PATENT NO. : 5,439,448
DATED : August 8, 1995
INVENTOR(S) : BORIS LESCHINSKY ET AL.

It is certified that error appears in the above-identified patent and that said Letters Patent is hereby corrected as shown below:

COLUMN 13

Line 16, "second tube" should read --second tube 512--.

COLUMN 15

Line 5, "clinical" should read --clinician--;
    Line 44, "port" should read --chamber--; and
    Line 49, "port" should read --chamber--.

COLUMN 17

Line 1, "first assembly" should read
      --first tube assembly--.

Signed and Sealed this

Fourth Day of May, 1999

Attest:

Q. TODD DICKINSON

Attesting Officer     Acting Commissioner of Patents and Trademarks